United States Patent
Chai

(12) 
(10) Patent No.: US 6,615,197 B1
(45) Date of Patent: Sep. 2, 2003

(54) BRAIN PROGRAMMER FOR INCREASING HUMAN INFORMATION PROCESSING CAPACITY

(76) Inventor: Songhai Chai, 1526 E. 32nd St., Cleveland, OH (US) 44114

( * ) Notice: Subject to any disclaimer, the term of this patent is extended or adjusted under 35 U.S.C. 154(b) by 0 days.

(21) Appl. No.: 09/523,938

(22) Filed: Mar. 13, 2000

(51) Int. Cl.$^7$ .......................... G06F 15/18; A61M 21/00
(52) U.S. Cl. ..................... 706/14; 706/911; 706/924; 600/27
(58) Field of Search ................. 706/15, 14, 924, 706/911, 903; 600/27, 26

(56) References Cited

U.S. PATENT DOCUMENTS

| | | | | |
|---|---|---|---|---|
| 3,782,006 A | * | 1/1974 | Symmes | 434/236 |
| 3,826,250 A | * | 7/1974 | Adams | 601/16 |
| 4,140,997 A | * | 2/1979 | Brady | 600/545 |
| 4,227,516 A | * | 10/1980 | Meland et al. | 600/26 |
| 4,289,121 A | * | 9/1981 | Kupriyanovich | 600/27 |
| 4,315,502 A | * | 2/1982 | Gorges | 600/27 |
| 4,354,505 A | * | 10/1982 | Shiga | 600/545 |
| 4,388,918 A | * | 6/1983 | Filley | 600/27 |
| 4,632,126 A | * | 12/1986 | Aguilar | 600/545 |
| 4,640,266 A | * | 2/1987 | Levy | 600/27 |
| 4,665,926 A | * | 5/1987 | Leuner et al. | 600/529 |
| 4,776,323 A | * | 10/1988 | Spector | 601/23 |
| 4,777,937 A | * | 10/1988 | Rush et al. | 600/27 |
| 4,902,274 A | * | 2/1990 | Gleeson, III | 600/27 |
| 5,036,858 A | * | 8/1991 | Carter et al. | 600/545 |
| 5,076,281 A | * | 12/1991 | Gavish | 600/534 |
| 5,101,810 A | * | 4/1992 | Skille et al. | 601/47 |
| 5,147,205 A | * | 9/1992 | Gross et al. | 345/581 |
| 5,149,317 A | * | 9/1992 | Robinson | 600/27 |
| 5,219,322 A | * | 6/1993 | Weathers | 600/27 |
| 5,304,112 A | * | 4/1994 | Mrklas et al. | 600/27 |
| 5,330,414 A | * | 7/1994 | Yasushi | 600/27 |
| 5,409,445 A | * | 4/1995 | Rubins | 600/27 |
| 5,518,497 A | * | 5/1996 | Widjaja et al. | 600/27 |
| 5,577,990 A | * | 11/1996 | Widjaja et al. | 600/27 |
| 5,595,488 A | * | 1/1997 | Gozlan et al. | 434/236 |
| 5,599,274 A | * | 2/1997 | Widjaja et al. | 600/27 |
| 5,613,498 A | * | 3/1997 | Yasushi et al. | 600/544 |
| 5,710,820 A | * | 1/1998 | Martin et al. | 381/321 |
| 5,725,472 A | * | 3/1998 | Weathers | 600/21 |
| 5,927,988 A | * | 7/1999 | Jenkins et al. | 434/116 |
| 6,019,607 A | * | 2/2000 | Jenkins et al. | 434/116 |
| 6,044,163 A | * | 3/2000 | Weinfurtner | 381/312 |
| 6,071,229 A | * | 6/2000 | Rubins | 600/27 |
| 6,146,147 A | * | 11/2000 | Wasowicz | 434/169 |
| 6,364,666 B1 | * | 4/2002 | Jenkins et al. | 434/156 |

\* cited by examiner

*Primary Examiner*—Emanuel Todd Voeltz
*Assistant Examiner*—Kelvin Booker
(74) *Attorney, Agent, or Firm*—Fay, Sharpe, Fagan, Minnich & McKee, LLP

(57) ABSTRACT

The present invention is a signaling system for the improvement of cognitive performance and intelligence, including: a) a method for improving the human cognitive performance and intelligence through a signaling program, a sequence of signals, that is presented to a person, stored in his/her long term memory, and recalled as control signals to effect periodical changes in the chunk size and number of chunks and the percentage of active units in the model of neural representation, thus reducing internal noise, error rate (ER) and response time (RT); b) a Computerized Auditory Program (CAP), which is a recording of a combination of sequences of computer generated sound signals and verbal instructions and signals, and is used as the signaling program mentioned in a) above; and c) a reinforcement system which uses a sequence of vibratory, visual, auditory, or other types of stimulus pulses that are initially associated with the signaling program, for example CAP in one embodiment, through time-correlated presentation and are subsequently presented at intervals in time that are correlated with CAP after CAP presentation has stopped, thus constantly offsetting the dissipation of the CAP memory and maintaining and reinforcing the CAP effects over time.

20 Claims, 18 Drawing Sheets

BRAIN PROGRAMMER FOR INCREASING HUMAN INFORMATION PROCESSING CAPACITY

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

The present invention relates to a signaling system including a signaling program and an accompanying reinforcement system, which, when working together, will improve cognitive performance and intelligence in a human being, and which can be used for the improvement of cognition and intelligence in human beings in general, and for the treatment of inherent or acquired mental deficiency, mental degeneration associated with senility, Alzheimer's disease, dyslexia, acalculia, and similar conditions in particular. This system is based on a specific model of neural representation, e.g., 'billboard model', which sees percepts or concepts as images put up on a neural network composed of interconnected neurons. The present invention uses a sequence of control signals to direct and regulate the chunking behavior and percentage of active neurons in the network, periodically changing the chunk size and number of chunks and percent neurons "on", thus reducing internal noise in neural representation, and reducing error rate (ER) and response time (RT). In one embodiment of the present invention, the signaling program is a Computerized Auditory Program (CAP) that includes a sequence of computer generated sound signals and verbal signals as the control signals mentioned above. In addition, the present invention uses an accompanying reinforcement system that gives a person periodically occurring vibratory-, visual-, auditory-, or other types of stimulus pulses to maintain the effects of signaling program over time.

It is a well documented fact that efficiency of cognitive performance, as measured in response time (RT) and error rate (ER), is closely related to measures of intelligence. Speed of information processing, measured in terms of response time (RT in performance of tasks involving perception and memory, is related to general intelligence and to gains in mental test performance over time in younger people. In fact some measures of intelligence are based on the speed of information processing. Evidence from studies of the changes in cognitive performance seen in aging population suggests that the efficiency of processing is an important factor contributing to age-related differences in working memory. Differences in efficiency of information processing will be reflected directly in fluid intelligence, which represents the acquisition of new information, or the grasping of new relations and abstractions regarding known information, and their effects will cumulate over time to result in different measures of crystallized intelligence, which represents the accumulation of knowledge over life span of the individual and is measured, for example, in tests of vocabulary, of general information, and of achievement.

It has been proposed that a very low level psychophysical measure, inspection time, may provide us with insights into the fundamental nature of intelligence. The basic idea is that individual differences in intelligence may derive, in part, from differences in rate of intake and processing of very simple stimulus information. In special conditions such as dyslexia (impaired ability to read), acalculia (difficulty with arithmetic operations), mental deficiency, senile dementia, Alzheimer's disease, etc., efficiency of information processing is of crucial importance and sometimes will have immediate, even critical consequences. Any methods that would improve cognitive performance could be called treatment for these conditions in the truest sense of the word. Furthermore, such methods could improve human intelligence, which is based on, crystallized from, and manifested in different types of cognitive performance.

There has been extensive neuropsychological study of the effects of factors that deteriorate cognitive performance as measured with response time (RT) and error rate (ER), e.g. math anxiety, dual-task, psychological refractory period manipulation, aging, Alzheimer's disease, dyslexia, etc.

The relationship between cognitive performance and intelligence is illustrated in a special condition called math anxiety. Highly math anxious people tend to have their anxiety aroused when doing tasks involving numbers, their attention is turned to intrusive thoughts and worry, and there is an on-line reduction in the available working memory capacity, resulting in a longer reaction time (RT) and higher error rate (ER), especially in computations of multi-column numbers involving carrying or borrowing operations. These people tend to choose less courses involving math in school, and they are less competent with math, compared to people who are less math anxious.

In dual task conditions, a person performing two cognitive tasks simultaneously show higher RT and ER values than that obtained from single task performance.

In tests involving psychological refractory period method, two stimuli are presented one after the other in quick succession, so that the refractory period following the response to the first stimulus will adversely affect the response to the second stimulus in terms of RT and ER.

In Attention-Deficit/Hyperactivity Disorders (ADHD), the information processing efficiency is impaired. Treatment with psychostimulants can only produce short-term benefits. Since the present invention does not involve drugs, and its effects can be maintained over a long period of time without side effects, it can be used as an effective treatment for ADHD. People with other types of mental problems such as autism and schizophrenia can also be treated with the present invention.

Compared to younger people, older people, for example over 60 years of age, show higher RT and ER in cognitive tasks, such as mental arithmetic or word or letter processing, and these changes have been attributed to increased internal noise, or neural noise, which can be thought of as perturbation of visual or perceptual features, resulting in increased errors (ER) and need for rechecking, hence longer RT.

apart from genetic factors, ethnic and social-class differences and home environmental factors all contribute to observed IQ differences. A check list, called Home Observation for Measurement of the Environment (HOME), has been developed for gathering information about the quality of children's home lives. Several factors have been reported to be linked with mental development. In infancy, organization of the physical environment and variety in daily stimulation show strongest relationships with mental test scores. During the preschool years, warmth, stimulation of language and academic behavior, and provision of appropriate play materials are the best predictors. For economically disadvantaged preschoolers, Project. Head Start was initiated by the federal government in 1965, and is still a mechanism for early intervention today. But a consistent finding of research on Head Start and other preschool intervention is that almost all children experience an eventual washout effect. In other words, improvements in IQ and achievement do not last for more than a few years.

Previous inventions intended to affect human consciousness or behavior include the following:

U.S. Pat. No. 3,782,006 to Symmes et al. shows a means and a method for providing audio and electrical stimuli to an individual to build an aversion to undesirable habits.

U.S. Pat. No. 4,227,516 to Meland et al. provides an apparatus for the electrophysiological stimulation of a patient for creating an analgesic condition in the patient to induce sleep, treat psychosomatic disorders, and to aid in the induction of electrohypnosis and altered states of consciousness.

U.S. Pat. No. 4,315,502 to Gorges discloses a device for relaxing, stimulating and/or driving brain wave form function in a human subject.

U.S. Pat. No. 4,776,323 to Spector is a biofeedback system to train an exerciser while he carries out athletic activity.

U.S. Pat. No. 5,076,281 to Gavish describes an apparatus and a method for monitoring and modulating biorhythmic activity.

U.S. Pat. No. 5,101,810 to Skille et al. describes an apparatus and a method for providing therapeutic audio and vibratory stimulation to an individual.

U.S. Pat. No. 5,219,322 to Weathers describes a psychotherapy apparatus and method that provides treating of an undesirable emotional arousal of a patient through coordinated and controlled presentation of visual and auditory stimuli to the patient.

U.S. Pat. No. 5,304,112 to Mrklas et al. describes an integrated stress reduction system.

U.S. Pat. No. 5,595,488 to Gozlan et al. discloses a system for providing audio and tactile stimulation to a subject to improve his alertness.

There has been no method that could directly improve efficiency of cognitive performance in terms of response time (RT) and error rate (ER) through a reduction of internal noise in the neural representation in the central nervous system. The present invention, a signaling system for the improvement of human cognitive performance and intelligence, is the first successful method. In a recent study on 40 older and 40 younger adults, the present invention was tested in an experiment—control design, and was found to improve the performance of mental multiplication. The present invention had main effects in reducing RT, and interacted with age and factors of problem difficulty in predicting both RT and ER. In each case, the present invention offset effects of old age and problem difficulty. In other tasks, such as letter match (to decide if two letters presented on a computer screen is the same or different) and lexical decision (to decide if a string of letters is a true English word), the present invention also reduced RT and ER.

BRIEF SUMMERY OF THE INVENTION

It is an object of the invention to program the working of a human brain by means of a signaling program, which is a combination of a sequence of signals and verbal instructions and signals, and further which, when stored in a person's long term memory, will be recalled as a sequence of control signals that will direct the working of the person's mind in a predetermined sequence of steps, periodically changing the chunk size and number of chunks and percent neurons "On" in the neural network for representation, thus reducing internal noise, resulting in lower error rate (ER) and shorter response time (RT);

A second object of the invention is to maintain and renew the memory and effects of the signaling program over time after the actual presentation of the signaling program to a person has stopped through a reinforcement system, which includes a sequence of stimulus pulses that are initially associated with the signaling program through time-correlated presentation and are subsequently presented at certain intervals in time that are correlated with the signaling program.

BRIEF DESCRIPTION OF THE SEVERAL VIEWS OF THE DRAWING

The present invention will be more fully understood by reference to the following detailed description thereof when read in conjunction with the attached. drawings, and wherein:

In FIG. 4, the name "pulses B program" simply means "the other sequence of sound pulses", to distinguish it from CAP, the primary auditory program.

DETAILED DESCRIPTION OF THE INVENTION

Figure 1:
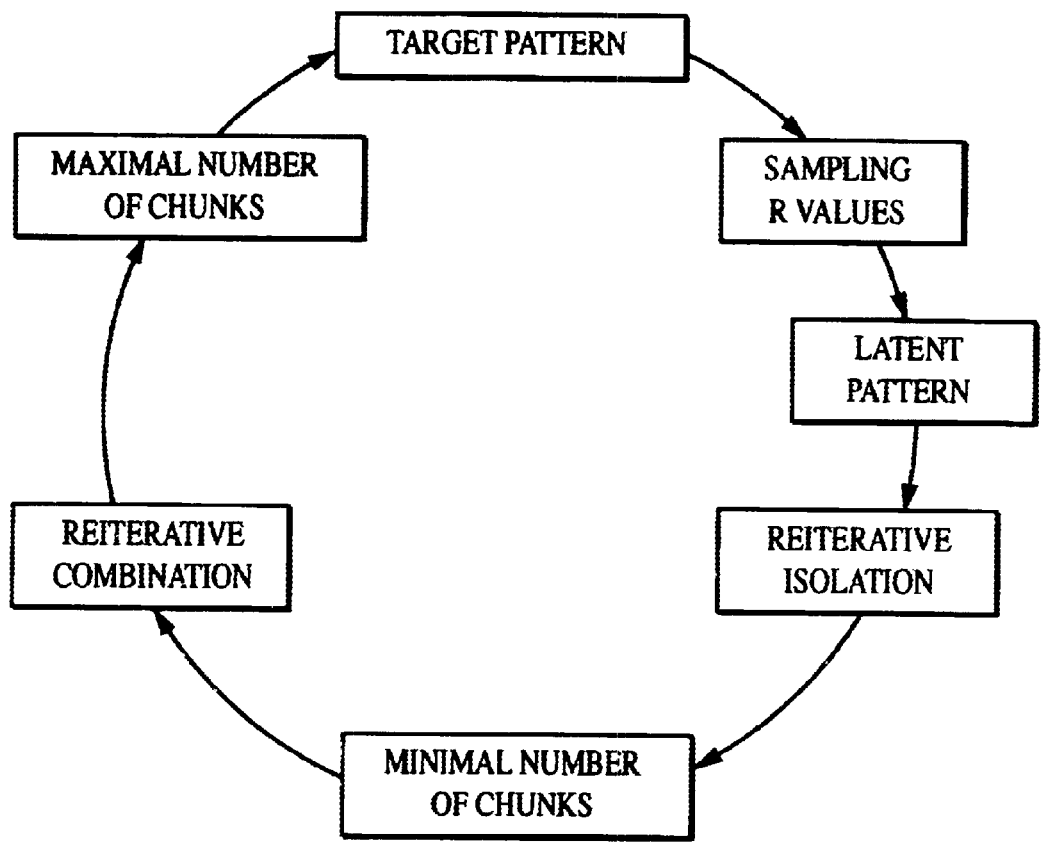
FIG. 1 is a flow-chart showing the main sequence of steps and operations involved in the signaling program, which is CAP in one embodiment. The steps follow one another in an endless circle, thus periodically changing the chunk size and number of chunks and the percentage of active neurons (represented by the R value) in the neural network for representation, resulting in reduced internal noise, error rate (ER) and response time (RT).

The present invention is based on a model of neural representation proposed by the inventor. For example, one such model is termed "billboard" model. The compilation of a signaling program is based on the following assumptions:

Any image or concept is registered, stored, and retrieved in a network of neurons in the central nervous system as a pattern of activities of these neurons. Each neuron can be either active or inactive, or "on" or "off", in the registration of a particular image. An image is registered as a pattern of this on-off states of the neurons, not the locus of any neuron in a particular state.

An apparent analogy is a billboard composed of many electric light bulbs. The image shown by the billboard can move around and still be recognized as the same image. An ideal system would be a billboard that is controlled by a central computer that can turn on or off each light bulb in an instant. In that case no meaningful changes in response time (RT) or error rate (ER) could be observed or manipulated. The problem is, the bulbs on the billboard are linked with synapses to one another, and the strengths of these synapses are modified with each presentation of an image. If two neurons are turned on simultaneously during an image, and if this pattern of activity is repeated a few times, they will tend to be turned on simultaneously by the synaptic transmission of the neural network, regardless of whether external demand calls for the "on" or "off" state. In other words, these two neurons can be viewed as a "chunk". In fact, each chunk can contain many neurons, and the synaptic linkage can be very strong, even permanent, as a result of long term experience and structural modification, especially in early life.

This synaptic modification and resultant "alliance", or "chunking" of neurons are both a blessing and a curse. They are the basic mechanism for memory. But if you have a strong memory for the old items, you will find it hard to learn new, because the establishment of a new pattern requires the modification of old patterns. Using our billboard analogy, suppose pattern A is a horse and pattern B a mule, we want to present pattern A and then pattern B sequentially. Obviously, A and B are very similar, they differ from each other by only a few light bulbs. If the light bulbs were independent from each other, after pattern A has been presented on the billboard, only a few bulbs would need to be turned on or off to change A to B. However, through repeated presentation of pattern A, all the light bulbs within pattern A have been formed into a chunk, and can only be turned on or off simultaneously when A is on. So these few bulbs can not be turned on or off on their own. You would have to turn off A completely before you can turn B on. So we see that patterns are easier to manipulate if they are composed of independent units.

However, if the units were completely independent from each other, there could be no master switch to turn A off or turn B on. You have to switch each individual light bulb on or off separately, a laborious and error prone process, since the system would have maximal entropy.

An obvious solution would be to change the "chunking" behavior of the system periodically, alternately making the whole billboard act as a single chunk at one moment and as a mass of independent bulbs at the next. The first job of a signaling program is to effect this periodical change. Suppose that at a certain point in time a control signal M will turn on an image on the billboard, image C, that has only one chunk. In other words, when image C is on, any part of the billboard can not be changed independently from other parts of the billboard. The whole billboard is a single chunk. Likewise, another control signal N will turn on the same image. Although control signals M and N induce the same image, the images induced by M and N can be viewed as separate and different entities, because they are induced by different control signals, and can be turned on or off independently. But they can not be turned on simultaneously on the billboard, since each image would require the concerted activities of all the light bulbs on the billboard. We label them as $C_1$ and $C_2$. Our task is to combine $C_1$ and $C_2$, or to turn them on simultaneously. When image $C_1$ is turned on, it will change slightly over time, so if $C_1$ is paired with two sequential control signals a and b for a few times, a and b will acquire the ability to induce slightly different versions of $C_1$, $C_{11}$ and $C_{12}$. These two versions of $C_1$ will have a common part which contain bulbs in the same on or off states regardless of which version is on, and one part each that is unique to either of them, containing light bulbs that must change their on—off states when the other version is turned on. Likewise we make control signals c and d induce slightly different versions of $C_2$, $C_{21}$, $C_{22}$. When next the control signals a, b, c, d are paired with control signal M for n times each, the common part of $C_{11}$ and $C_{12}$, will be paired with M for 2*n times (n times from the pairing of M and a and n times from the pairing of M and b), whereas the unique parts of $C_{11}$ and $C_{12}$ Will be paired with M only n times each. The same is true for the common and unique parts of $C_{21}$ and $C_{22}$. As a result, the common parts between $C_{11}$ and $C_{12}$ and between $C_{21}$ and $C_{22}$ will form a stronger association with control signal M, and consequently be induced preferentially by M. And since each of these two common parts is only part of the original images $C_1$ or $C_2$, when they are on the billboard simultaneously, they together will take about the same number of bulbs that had been taken by either $C_1$ or $C_2$ alone before this process. Now when M is on, it will induce $C_1$ and $C_2$ as two separate entities on the billboard. In other words, $C_1$ and $C_2$ have been combined.

Since $C_1$ and $C_2$ are the same image, we can say that after this procedure, M still induces C, but a C that is composed of two parts. Since these two parts can be manipulated independently, what we get is an increase in the number of "chunks" on the billboard. The number of chunks is an analogy to a concept in statistics, namely, the degrees of freedom, which indicate how many parts you can change without changing other parts. After this combination process, the number of chunks is doubled. This whole process can be repeated many times, resulting in a large number of chunks, or degrees of freedom. To reduce the degrees of freedom, we just combine C with a blank. We pair control signals a and b with C, and c and d with a blank, that is, present c and d without any particular event, and then pair a, b, c, d with M. After this process, only a half of the chunks in C are linked with M, so the degrees of freedom are halved. Since this process is the opposite of combination, we can call it "isolation". This process of isolation is repeated the same number of times as that for combination, and the reiterative isolation and combination processes follow one another endlessly, thus achieving the periodic change of chunking behavior of the system, as shown in FIG. 1.

When the chunking behavior can be manipulated in this way, an obvious question would arise: If the target pattern is B, can we anticipate its occurrence and present a "latent" pattern A at the right time, so that only a few minor changes would be required to modify A into B? The phrase "a few minor changes" implies similarity, but how is similarity defined? Using the horse—mule analogy, we can see that no matter at what location on the billboard they are presented, one quantity would remain constant and similar between these two patterns, namely, the percentage of light bulbs on. In the absence of other clues, I suggest that a defining variable of a pattern is R, the percentage of bulbs on, and further, that when the individual bulbs can be manipulated independently, the difference between two patterns is the difference between the two values of R.

suppose that when no patterns are being presented, background "noise" causes the bulbs on the billboard to be turned on and off randomly. When most of the bulbs have been turned off and left alone, an increasing number of bulbs will turn themselves on spontaneously, so the percentage of bulbs on, R, will increase gradually. Then R becomes a function of time. At a certain time this value will be the R value for pattern A. If a control signal S is presented at this time, and this whole process is repeated for a few times, S will acquire the ability to induce a distribution of bulbs in the "on" and "off" states on the billboard that corresponds to pattern A, which can be transformed into pattern B with only minor modifications.

The next question would be, how can you anticipate pattern A and its R value? The answer lies in the fact that if you continuously sample a few discrete R values distributed evenly in the limited range of possible R values (0–1), you are bound to get an R value that you can name as R value for A, since it would be close to the R value of B. The second job of a signaling program is to get pattern A by periodically sampling R values, as shown in FIG. 1. As can be seen in FIG. 1, a sampled R value gives rise to a latent pattern, or pattern A, which is then subjected to reiterative isolation to reduce the chunk number to a minimum, that is one, or unity, that is to say the whole billboard is a single chunk, so that every part of the billboard will be easily controlled by a master switch. Then this chunk, is combined with itself, and reiterative combination process will lead to a maximal number of chunks, each of which is a unit, or bulb of the billboard and can be turned on or off independently.

Consequently, this latent pattern comprising a maximal number of chunks can easily be modified to become a target pattern, or pattern B, which is what we want to put up on the billboard. Then this target pattern will lead to another R value being sampled, and the whole process repeats itself. This cyclic process runs over and over, each cycle giving rise to a different latent pattern A and a different target pattern B. What we get as a result is a succession of target patterns that are exactly what we want to put up on the billboard one after another, or a thought process. Since the target patterns have a maximal number of chunks that can be controlled individually, these target patterns are more precise, have less internal noise or perturbation, and take less time to put up on the billboard than a succession of patterns put up on the billboard in the absence of a signaling program described by the present invention.

Figure 2:
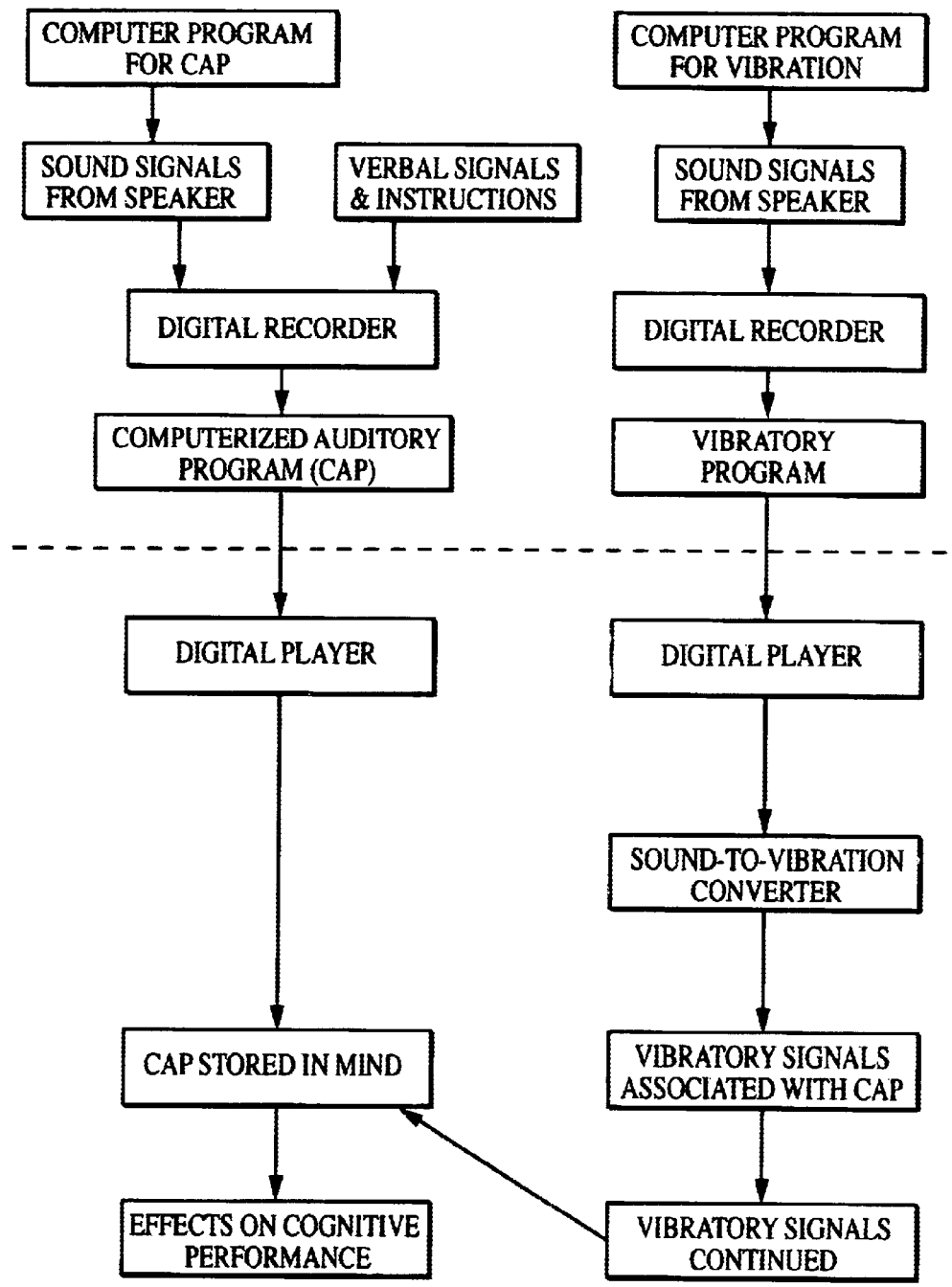
FIGS. 2, 3 and 4 are flow charts showing the steps involved in the production (above the broken line) and application (below the broken line) of CAP and the accompanying reinforcement system in the three embodiments of the invention using CAP as the signaling program and vibratory, visual, and auditory reinforcing pulses, respectively, in the reinforcement system.
Figure 3:
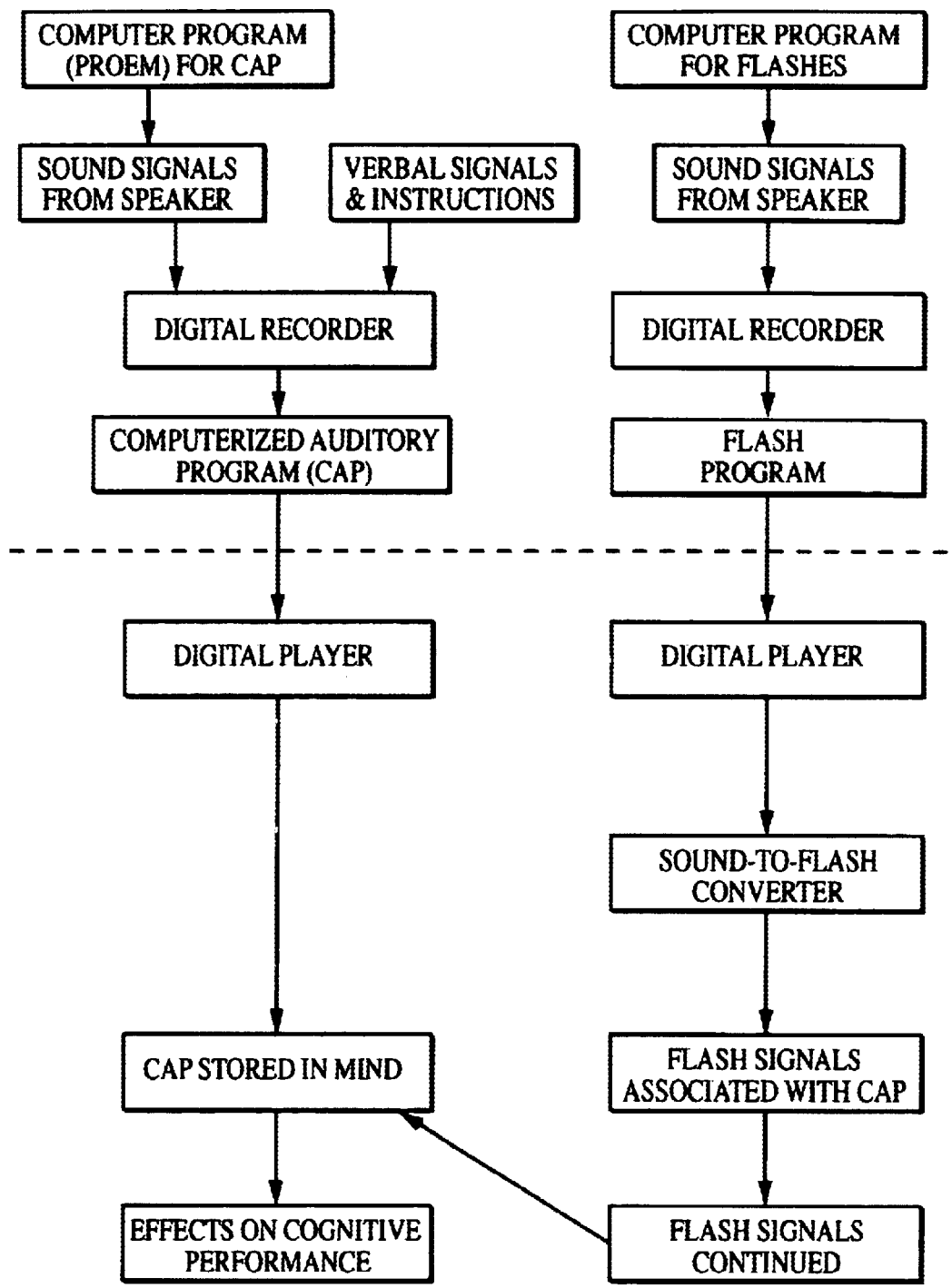
Figure 4:
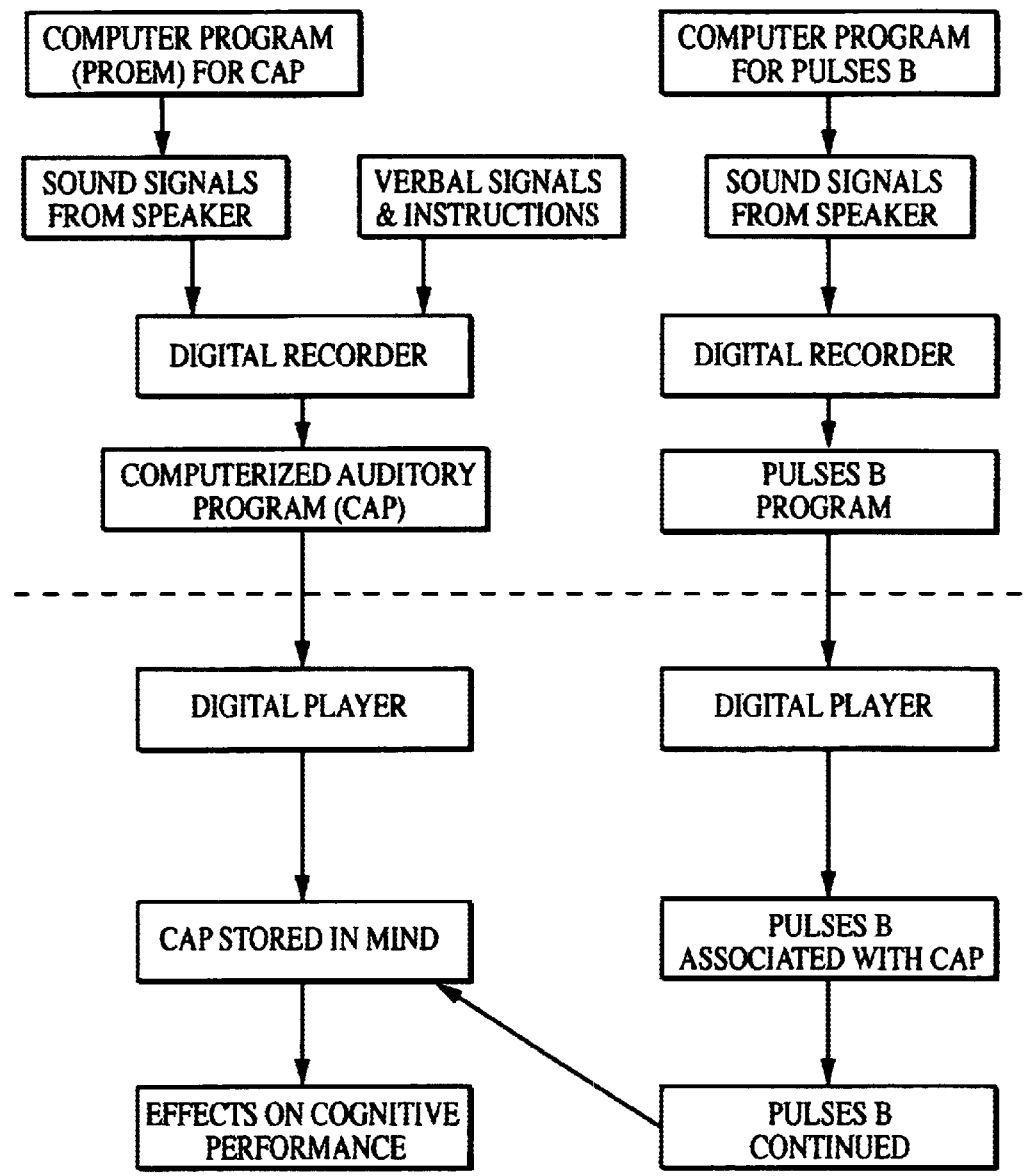

The signaling program of the present invention can take different forms, using different kinds of signals as control signals, so long as the control signals are arranged in such a sequence as to do the two jobs described above: 1) periodically changing the chunk size and number of chunks; and 2) periodically changing the percentage of neurons "on". In the case of Computerized Auditory Program (CAP) as the signaling program, the control signals mentioned above are sound signals generated by a personal computer. The frequencies of these signals are their identities, and the particular sequence and timing of their presentation are controlled precisely by a program written in GW-basic, entitled "Proem" (Copyright TXu 736-927, Apr. 19, 1996, Songhai Chai). The steps involved in the production of CAP are shown in FIGS. 2, 3 and 4, on the left side of these figures, above the broken line. The sound signals from the speaker of a personal computer running "Proem" are recorded on a digital audio recorder, and then combined With verbal instructions and signals to form CAP (Copyright SRu 276-318, Apr. 19, 1996, Songhai Chai).

When it is time to use the signaling system to improve cognitive performance and intelligence, the whole signaling program is presented to a person in its entirety before he/she begins a task requiring cognition and intelligence. In the case of CAP as the signaling program, CAP is played back to a person through a pair of headphones or a speaker. The whole CAP lasts about 31 minutes.

As shown on the left side of FIGS. 2, 3 and 4 below the broken line, when a person is listening to CAP, the sound signals of CAP are stored in his/her long term memory (LTM). After he/she has finished listening to the complete CAP, these sound signals can be recalled from LTM in the original order of presentation. In other words, the person can relive the CAP in its entirety. Since the sound signals of CAP are arranged in an endless circle shown in FIG. 1, the complete sequence of CAP can be recalled repeatedly, and these periodically recalled sound signals act as control signals and exert their effects on the cognitive performance over and over.

Gradually, the memory of the signaling program would fade away, or be forgotten. To maintain and renew the memory and the effects of the signaling program over time, a concomitant sequence of stimulus pulses is used, and is called a reinforcement system. The stimulus pulses of this system acquire the ability to renew the memory of the signaling program through initial time-correlated presentation of both the signaling program and these pulses. After the completion of the presentation of the signaling program, these stimulus pulses were presented at certain intervals in time that are correlated with the signaling program, thereby constantly renewing and maintaining the memory and effects of the signaling program. The ability of these stimulus pulses to renew and maintain the memory and effects of the signaling program is not decreased with repeated presentation of these pulses because the information needed to preserve this ability is contained in the time intervals of their presentation that are correlated with the signaling program, and these time intervals are preserved truthfully by the reinforcement system, and the information contained in these time intervals is constantly provided and used to maintain the association between these stimulus pulses and the signaling program.

In the embodiments of the invention described in detail in this specification, a brief (less than one second) low frequency vibratory signal, a flash of light, a sound pulse, or another type of stimulus is given to the subject at certain points in time. The presentation of these pulses of stimulus is controlled by another program run synchronously with CAP, and is a recording of sound pulses at certain intervals in time that are correlated with CAP. This accompanying program is called vibratory program, flash program, or pulses B program in the embodiments of the invention using vibratory, visual, or auditory reinforcing pulses, respectively, as shown on the right side of FIGS. 2, 3 and 4. The name "pulses B program" simply means "the other sequence of sound pulses", to distinguish it from CAP, the primary auditory program. On the right side of FIGS. 2, 3 and 4, steps above the broken line are those for the production of this accompanying program, and the steps below the broken line are those for the application of this program in coordination with CAP. This low frequency vibration stimulus, flash of light, sound pulse, or another type of stimulus is initially associated with CAP through time-correlated presentation. Then, after CAP playback has stopped, the vibration stimulus, flash of light, sound pulse, or another type of stimulus is repeated periodically, refreshing the memory of CAP, maintaining its effects while he/she is performing some cognitive task, such as reading a book. The vibrators, light emitting diodes (LEDs) or another type of lights, or a device giving out another type of stimulus are driven by a brief audio frequency electric pulse through an electronic circuit shown in FIG. 5. These conversion mechanisms are named "sound-to-vibration converter" or "sound-to-flash converter" in FIGS. 2 and 3. In the alternative embodiment of the invention using auditory reinforcing pulses, such electronic circuit is not necessary, as the brief audio frequency electric pulses can be converted into auditory reinforcing pulses directly through a pair of headphones or a speaker, as shown in FIG. 4. These audio frequency pulses are generated by another digital audio player playing back the accompanying program that is synchronized with the one that plays back CAP. The reinforcing pulses of vibration, light, sound, or another type of stimulus act just as a signal to induce another event, in this case the memory of CAP, in a person's mind. This periodical repetition of a signal that has been associated with CAP would counteract the dissipation of memory of CAP over time. Vibratory instead of visual or auditory reinforcing pulses were uses in the first study because compared to other sensory modalities, vibration is less distracting when the subject is performing cognitive tasks.

Figure 6:
FIG. 6 shows the first step in the production of the computerized signaling program, for example CAP in one embodiment, or an accompanying reinforcement system using computer generated pulses, compilation of a computer program and loading the program in a computer 1.
Figure 7:
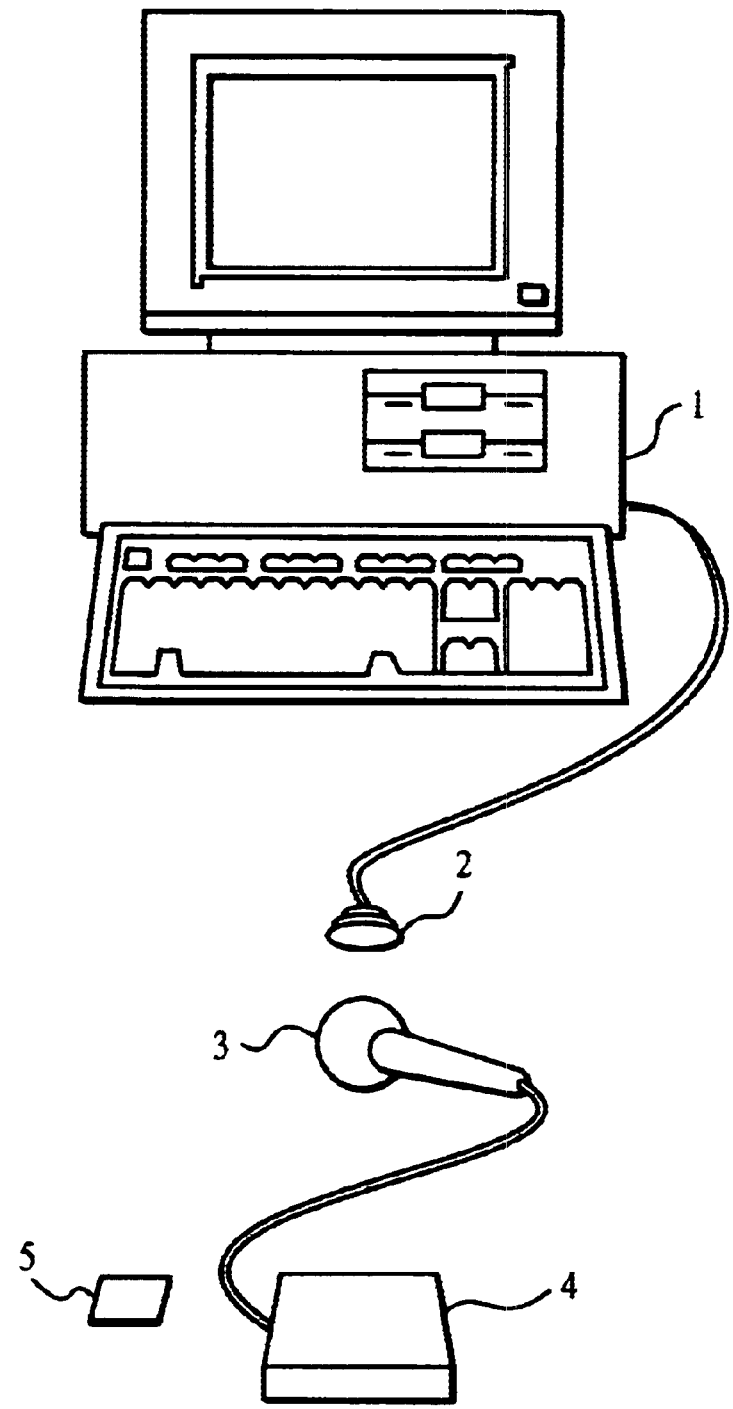
FIGS. 7 and 8 show the second step in the production of CAP, recording of sequences of sound signals from a speaker 2 of a computer 1 running the program, entitled "Proem" (FIG. 7), and verbal signals and instructions (FIG. 8) on a digital audio recorder 4 through a microphone 3, resulting in a recording of the CAP 5.
Figure 8:
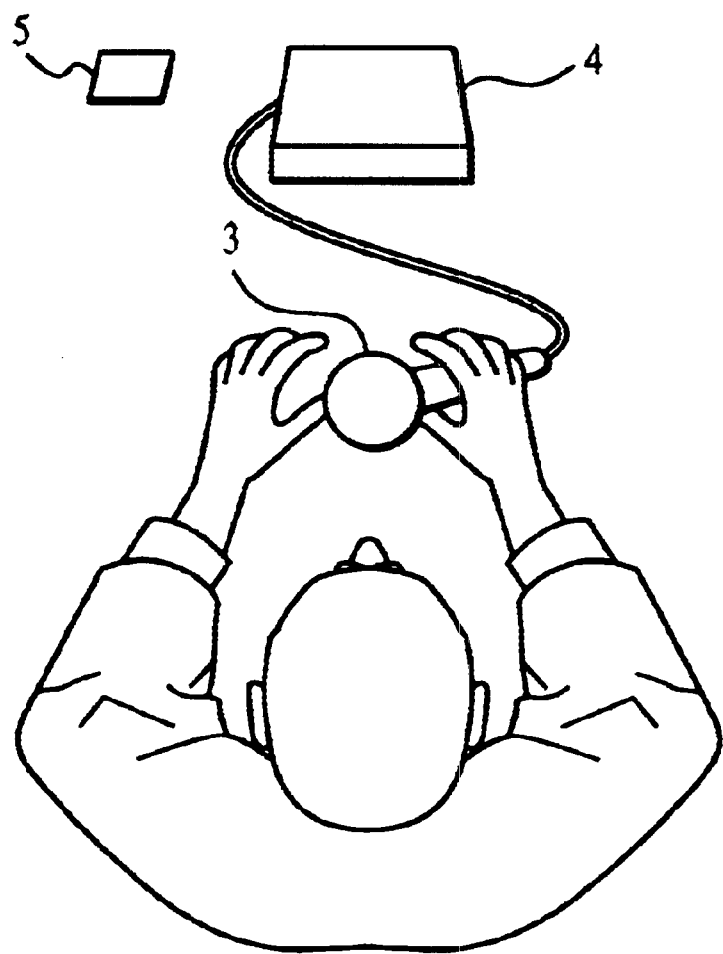

The production process of CAP is shown in FIGS. 6–8. A computer program written in GW-BASIC, entitled "Proem" (Copyright TXu 736-927, Apr. 19, 1996, Songhai Chai), is loaded into a personal computer 1, and when run, generates a sequence of sound signals through a speaker 2. This sequence of sound signals and additional verbal instructions and signals are recorded by a digital audio recorder 4 through a microphone 3, resulting in a recording 5, called Computerized Auditory Program (CAP, Copyright SRu 276-318, Apr. 19, 1996, Songhai Chai).

Figure 9:
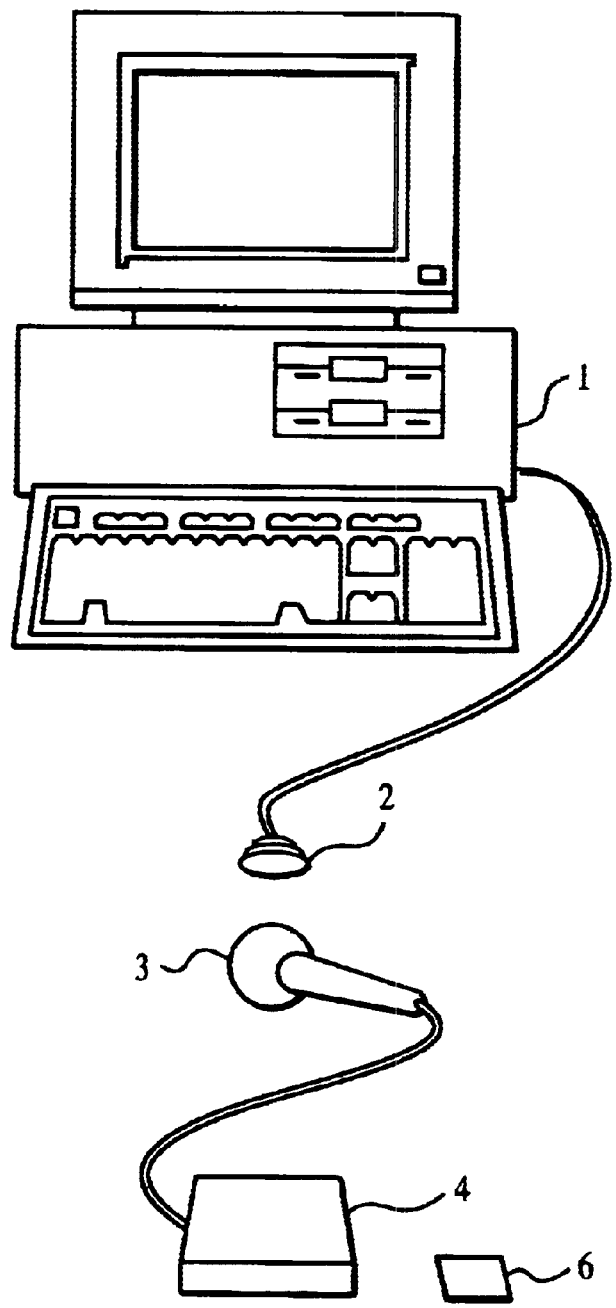
FIG. 9 shows the second step in the production of the accompanying reinforcement system using vibratory, visual, auditory, or other types of pulses, the recording of a sequence of sound pulses at certain intervals in time from a speaker 2 of a computer 1 running the accompanying program on a digital audio recorder 4 through a microphone 3, resulting in an accompanying audio recording 6, which is called "vibratory program", "flash program", or "pulses B program" in the embodiment using vibratory, visual, or auditory reinforcing pulses, respectively. The name "pulses B program" simply means "the other sequence of sound pulses", to distinguish it from CAP, the primary auditory program.

As shown in FIG. 9, a second sequence of sound pulses of less than 1 second duration at certain intervals in time is generated by a computer 1 through a speaker 2, and is recorded by a digital audio recorder 4 through a microphone 3, resulting in a recording 6, which is called vibratory program, flash program, or pulses B program in the embodiments of the invention using vibratory, visual, or auditory reinforcing pulses, respectively.

Figure 10:
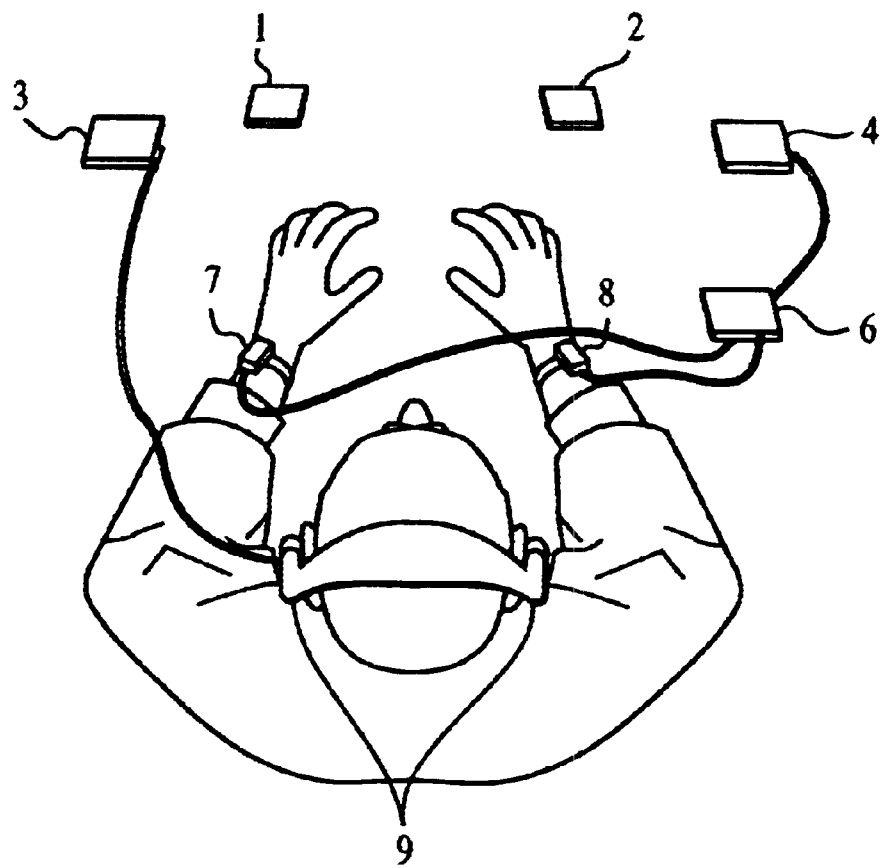
FIG. 10 shows the first step in the application of the embodiment of the invention using CAP as the signaling program and vibratory reinforcing pulses, the time-correlated presentation of CAP 5 and vibratory program 6 respectively by a digital audio player 7 through a pair of headphones 9 and by another digital audio player 8 through an electronic circuit 10 and a pair of vibrators 11 and 12 attached to a person's wrists.
Figure 11:
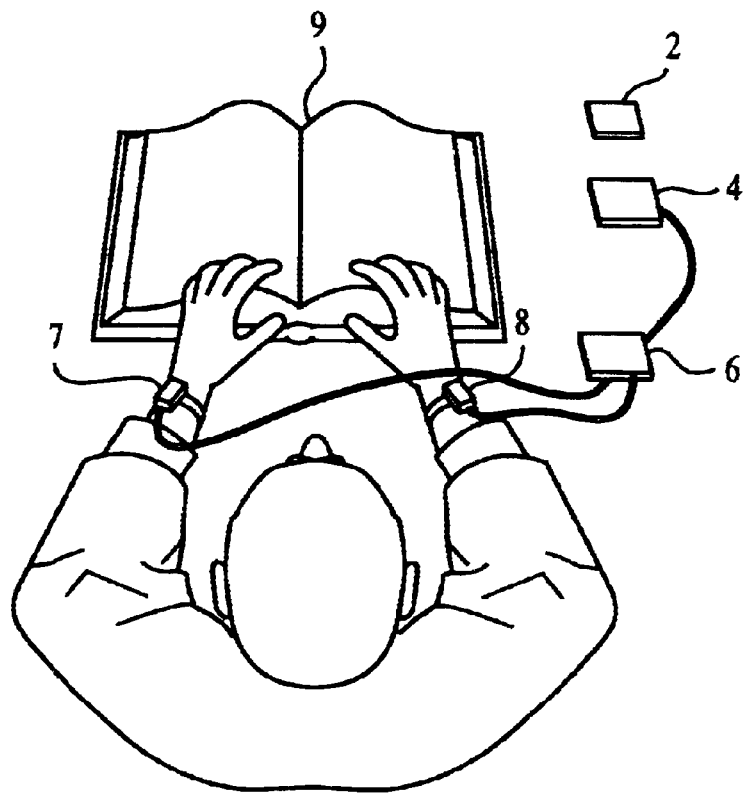
FIG. 11 shows the second step in the application of the embodiment of the invention using vibratory reinforcing pulses, continued presentation of only vibratory reinforcing pulses at certain intervals in time by a digital player 8 playing the vibratory program 6 through an electronic circuit 10 and a pair of vibrators 11 and 12 attached to a person's wrists while he/she is performing a cognitive task, in this example reading a book 13.
Figure 12:
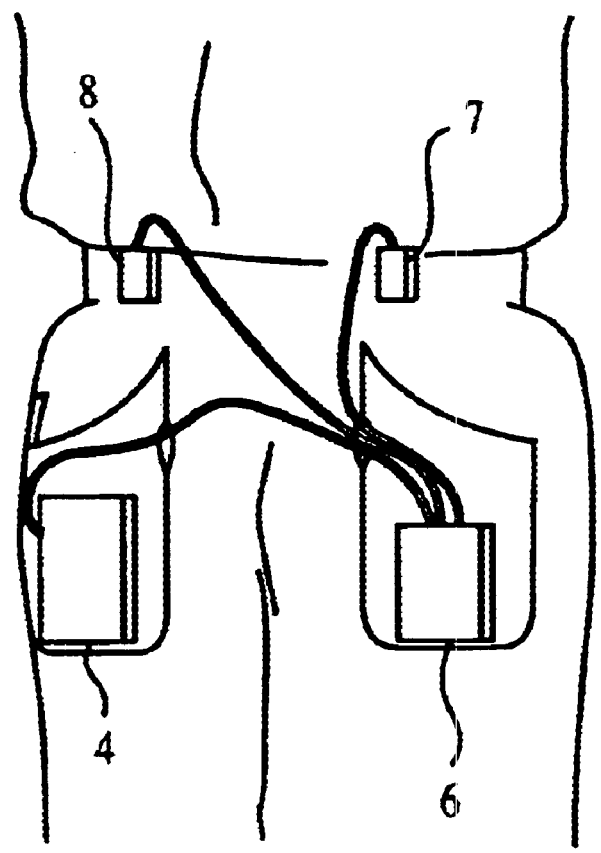
FIG. 12 shows another method of attaching the vibrators 11 and 12 to a person's body, in this example tucked under his/her belt, and carrying the digital player 8 for the vibratory program and a box containing the electronic circuit 10.
Figure 13:
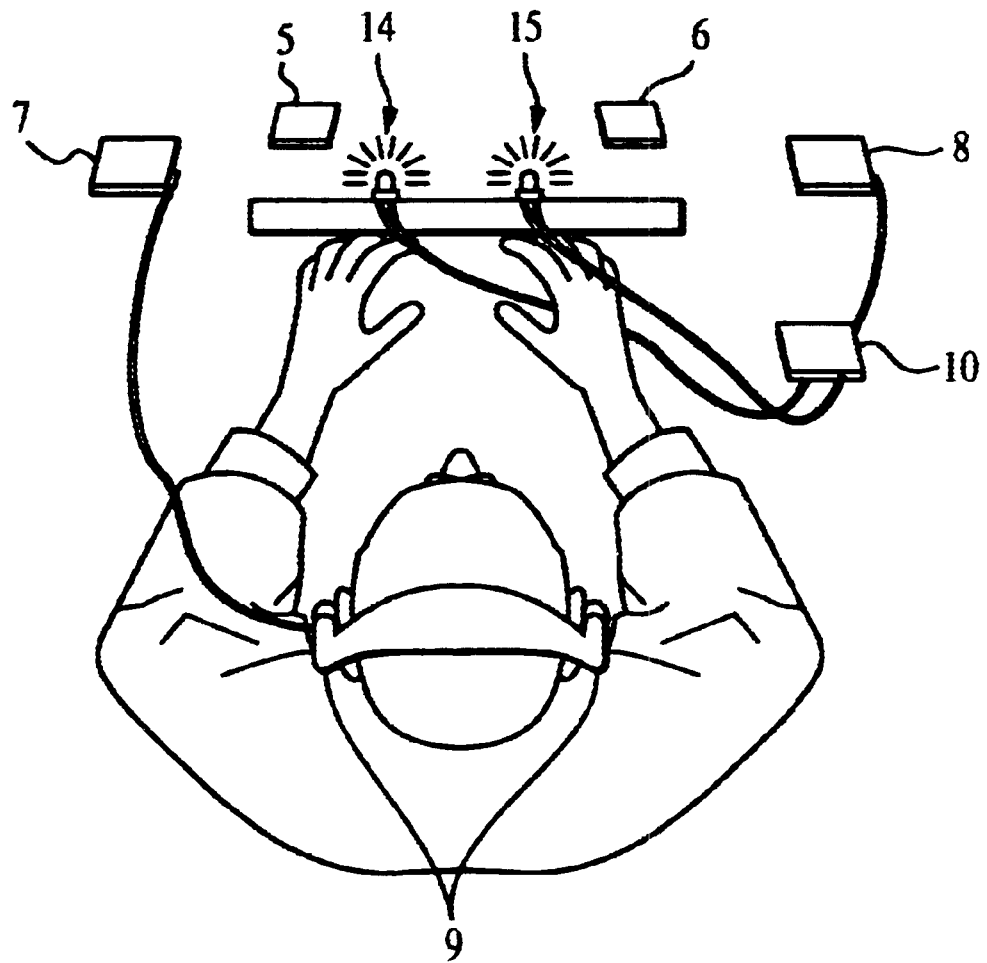
FIG. 13 shows the first step in the application of the embodiment of the invention using CAP as the signaling program and visual reinforcing pulses, the time-correlated presentation of CAP 5 and flash program 6 respectively by a digital audio player 7 through a pair of headphones 9 and by another digital audio player 8 through an electronic circuit 10 and a pair of light emitting diode (LEDs) 14 and 15, in this example attached to a transparent ruler placed in front of the person in such a manner that the two LEDs appear in symmetrical or conjugal positions in the left and right peripheral field of vision. The LEDs can be attached to a pair of spectacles and seen through an optical system by the person in his/her peripheral field of vision.
Figure 14:
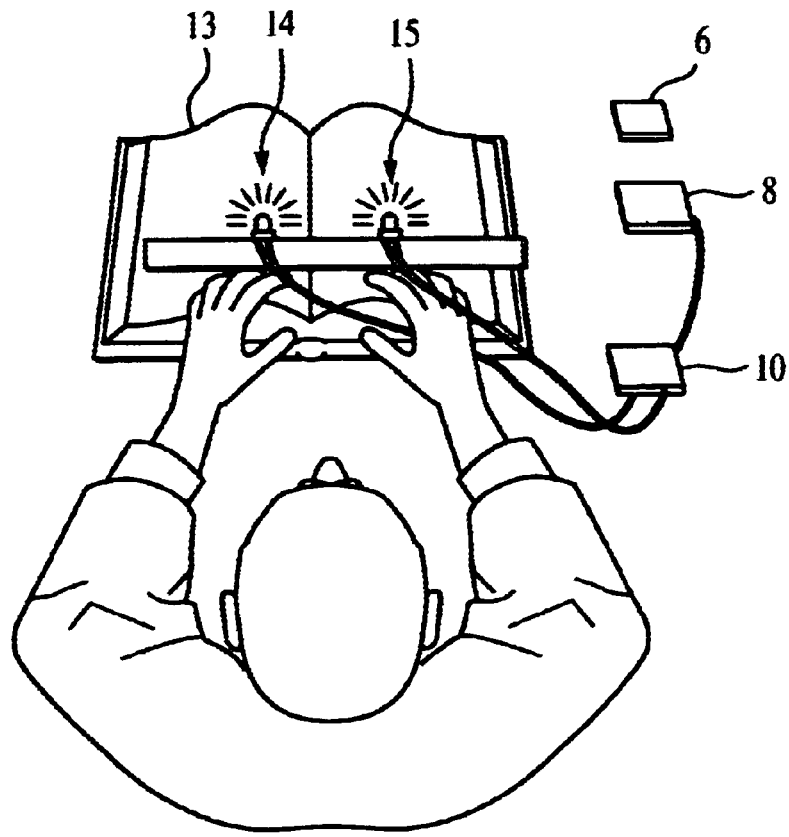
FIG. 14 shows the second step in the application of the embodiment of the invention using visual reinforcing pulses, continued presentation of only visual reinforcing pulses at certain intervals in time by a digital player 8 playing the flash program 6 through an electronic circuit 10 and a pair of LEDs 14 and 15, in this example attached to a transparent ruler placed in front of the person in such a manner that the two LEDs appear in the same symmetrical, or conjugal positions in the left and right peripheral field of vision as those in the first step shown in FIG. 13, while he/she is performing a cognitive task, in this example reading a book 13, using the central part of the field of vision. The LEDs can be attached to a pair of spectacles and seen through an optical system by the person in his/her peripheral field of vision simultaneously with visual presentation of the cognitive task appearing in the center of the field of vision.

The application of the embodiments of the present invention using CAP as the signaling program is shown in FIGS. 10–18, where FIGS. 10–12 show the application of the embodiment of the invention using vibratory reinforcing pulses, FIGS. 13 and 14 show the application of the embodiment of the invention using visual reinforcing pulses, and FIGS. 15–18 show the application of the embodiment of the invention using auditory reinforcing pulses. As shown in FIGS. 10, 13, 15, and 17, CAP 5 is played back by a digital player 7 to a person through a pair of headphones 9 or a speaker 16, and is stored in his/her long-term memory (LTM), and, when he/she is subsequently performing cognitive tasks, exemplified in FIGS. 11, 14, 16, and 18 as reading a book 13, will be recalled as a sequence of control signals described above that will achieve the steps and operations shown in FIG. 1.

Figure 5:
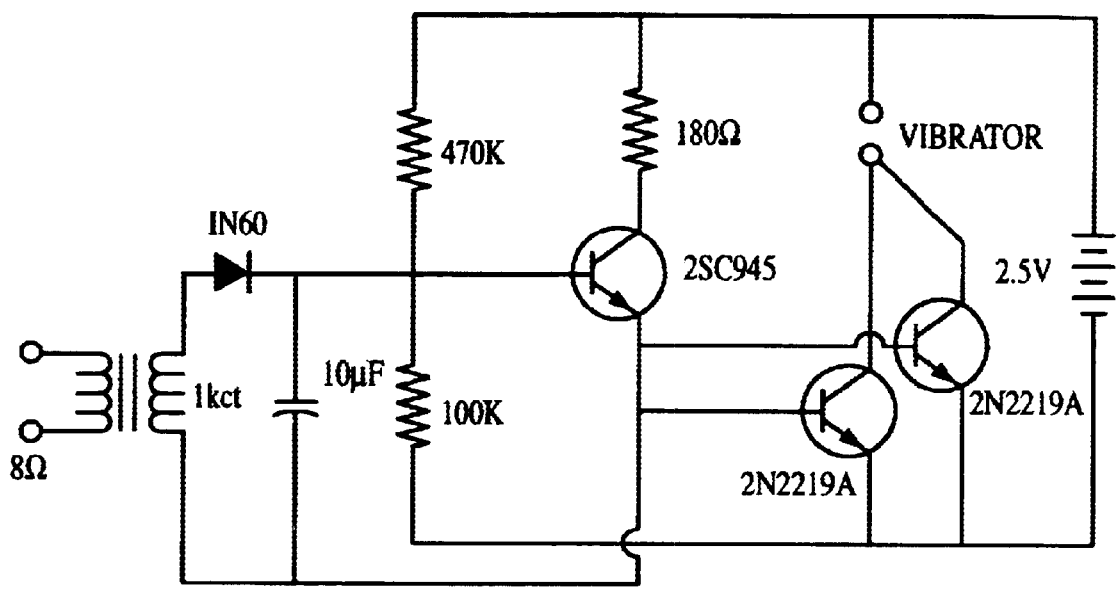
FIG. 5 is a diagram of an electronic circuit for the conversion of audio frequency electrical pulses into direct current pulses. Two identical sets of such circuit as shown in the figure drive two vibrators attached to a persons body or two light emitting diodes (LEDs) or other types of lights seen in the persons peripheral field of vision, or devices giving out other types of stimulus, and are part 10 of the following figures.

In the embodiment of the invention using vibratory reinforcing pulses, vibratory program 6 is played back by a digital player 8, that is synchronized with digital player 7 that plays back CAP 5, as shown in FIG. 10. The sequence of sound pulses from player 8 playing back vibratory program 6 are converted into a sequence of direct current pulses by an electronic circuit 10, which consists of two identical parts, one for each vibrator. One of the two parts is illustrated in FIG. 5. These direct current pulses drive a pair of vibrators 11 and 12 attached to the same persons body, giving a sequence of low frequency vibratory signals of less than 1 second duration at the same intervals in time as that of the sound pulses from player 8. The digital players 7 and 8 are synchronized, so that the low frequency vibratory signals are initially associated with CAP through time-correlated presentation, and, as shown in FIG. 11, when player 7 has stopped and player 8 continues playing back vibratory program 6 repeatedly, will periodically occur at intervals that are time-correlated with CAP and constantly renew the memory of CAP in the person's mind, thus maintaining CAP effects over time while the person is performing a cognitive task, in this example reading a book 13. The vibrators can be attached to a person's body at any symmetrical places, for example tucked under the belt and separated from the skin by a layer of fabric of the T-shirt, as shown in FIG. 12.

In the embodiment of the invention using visual reinforcing pulses, the direct current pulses from electronic circuits 10 drive a pair of light emitting diodes (LEDs) 14 and 15 seen by the person at symmetrical, or conjugal positions in the left and right peripheral field of vision. The LEDs 14 and 15 can be attached to a pair of spectacles and seen through an optical system by the person in his/her peripheral field of vision. The digital player 8 playing back flash program 6 is initially synchronized with the digital player 7 playing back CAP 5, and continues to play back flash program 6 after CAP 5 has stopped and while the person is performing a cognitive task, in this example reading, a book 13, as shown in FIGS. 13 and 14.

Figure 15:
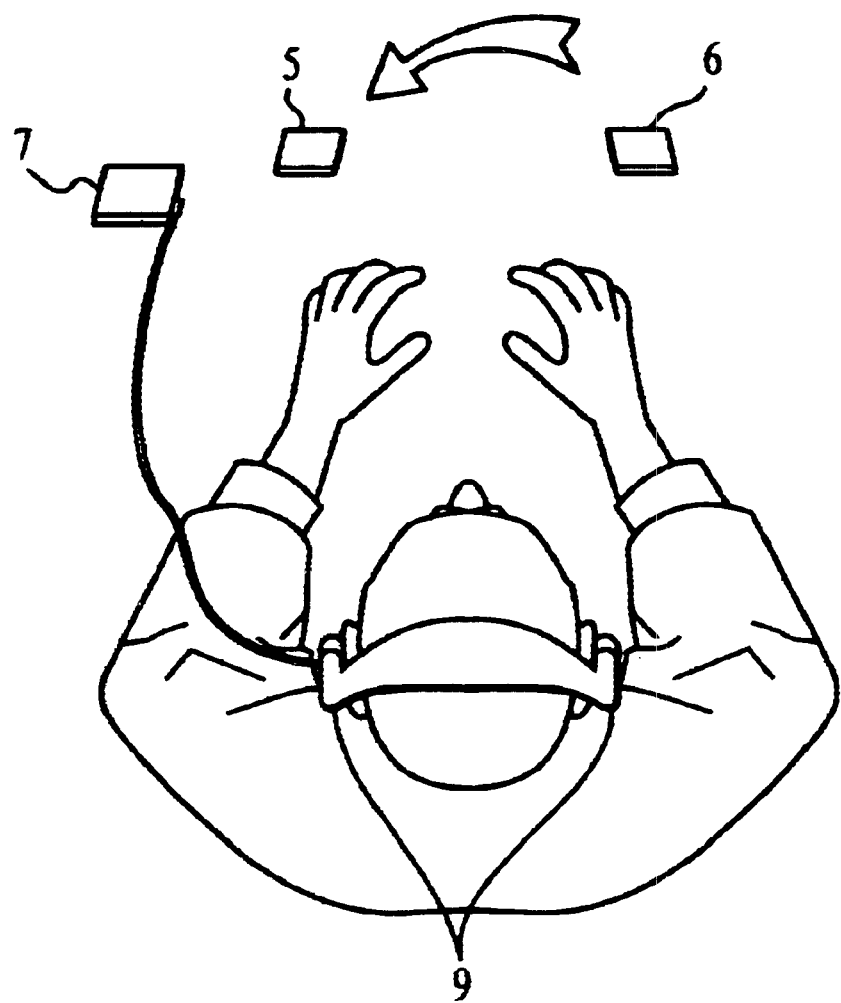
FIG. 15 shows the first step in the application of the embodiment of the invention using CAP as the signaling program and auditory reinforcing pulses, the time-correlated presentation of CAP 5 and pulses B program 6 by a digital audio player 7 through a pair of headphones 9. The CAP 5 and pulses B program 6 have been combined into a single recording whose first part is represented by recording 5 in this figure.
Figure 16:
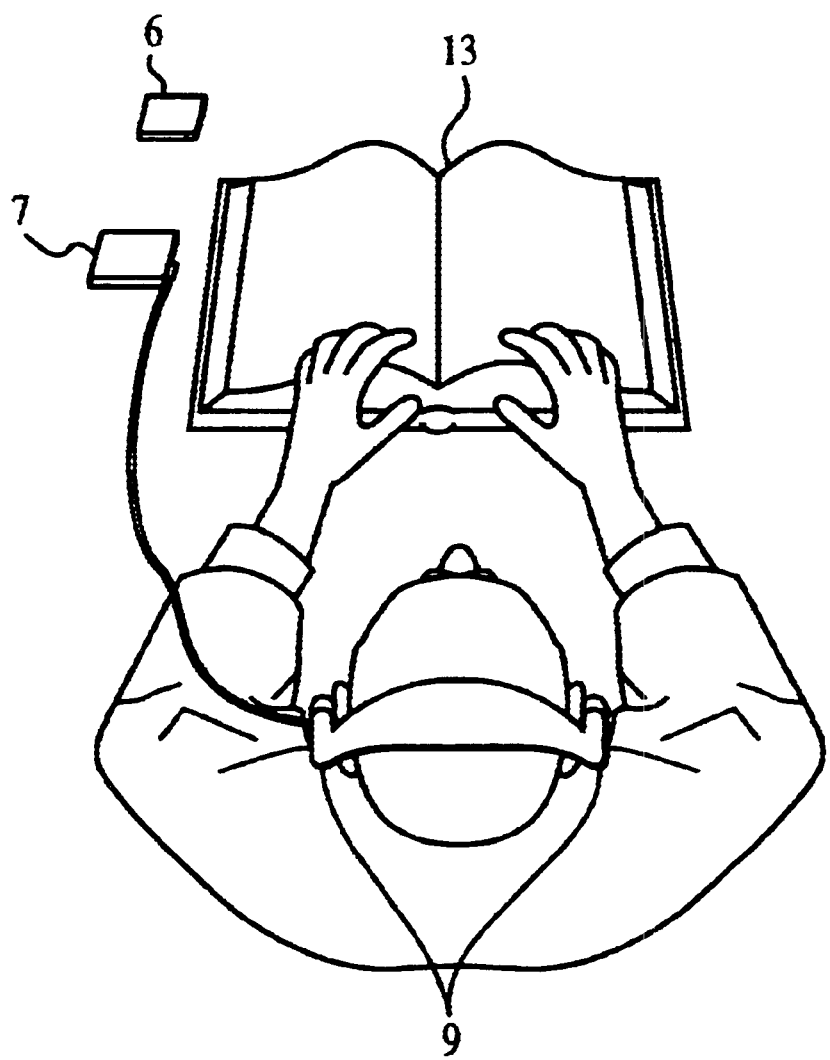
FIG. 16 shows the second step in the application of the embodiment of the invention using auditory reinforcing pulses, continued presentation of only auditory reinforcing pulses at certain intervals in time from pulses B program, which is the second part of the combined single recording described in the above paragraph for FIG. 15 and is represented by recording 6 in the present figure, by the same digital player 7 used in the first step through a pair of headphones 9, while he/she is performing a cognitive task, in this example reading a book 13.
Figure 17:
FIG. 17 shows the first step in the application of an alternative embodiment of the invention using CAP as the signaling program and auditory reinforcing pulses, in which both CAP and auditory reinforcing pulses from pulses B program are presented through a speaker instead of a pair of headphones, the time-correlated presentation of CAP 5 and pulses B program 6 respectively by a digital audio player 7 through a speaker 16 and by another digital audio player 8 through another speaker 17.
Figure 18:
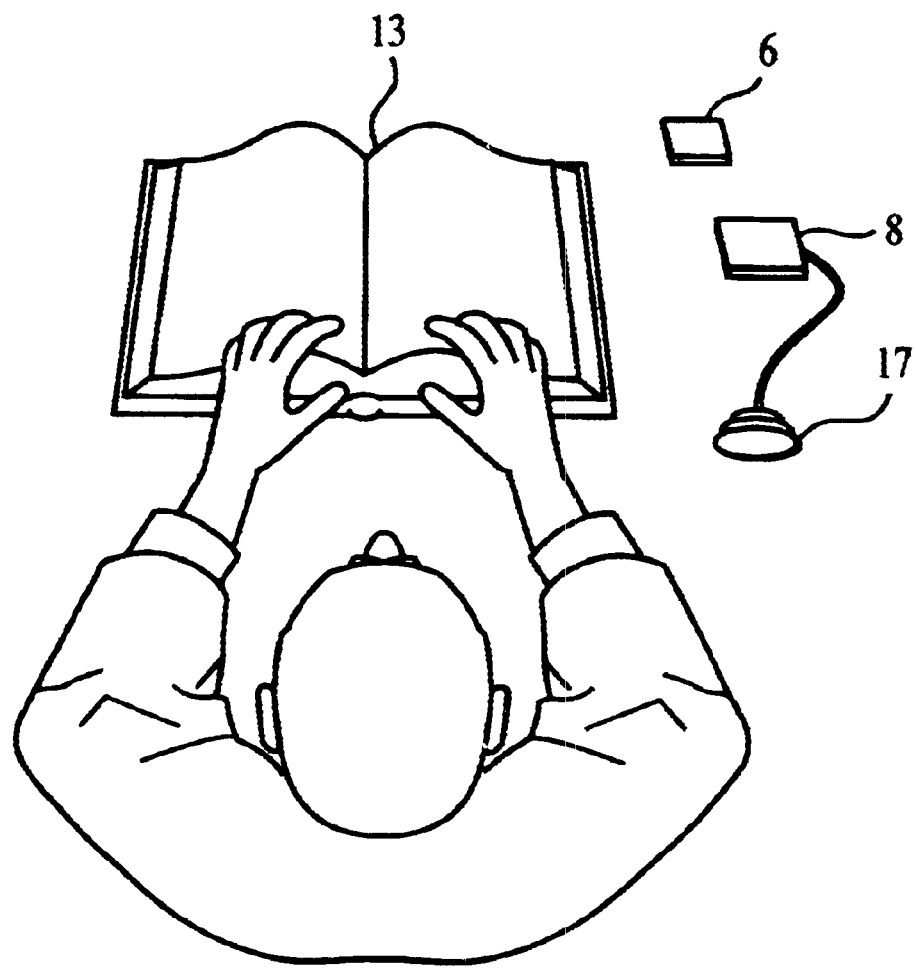
FIG. 18 shows the second step in the application of the alternative embodiment of the invention using auditory reinforcing pulses, in which both CAP and auditory reinforcing pulses are presented through a speaker instead of a pair of headphones, continued presentation of only auditory reinforcing pulses at certain intervals in time by a digital player 8 playing back the pulses B program 6 through a speaker 17, while he/she is performing a cognitive task, in this example reading a book 13.

In the embodiment of the invention using auditory reinforcing pulses, the CAP 5 is played back by a digital player 7 through a pair of headphones 9 or a speaker 16, as shown in FIGS. 15 and 17. The pulses B program 6 is played back by another digital player 8 through a speaker 17, as shown in FIGS, 17 and 18, or is combined with CAP 5 in a single recording and played back by the digital player 7, which first plays back the CAP 5 part of the combined recording, and continues to play that part of the combined recording that corresponds to pulses B program 6 after the CAP 5 part of the combined recording is over and while the person is performing a cognitive task, in this example reading a book 13, as shown in FIGS. 15 and 16.

What I claim as my invention is:

1. A method for improving the cognitive performance and intelligence of a person, the method including the following steps:
    a) playing a previously recorded audio sequence to the person prior to the person performing a task requiring cognition and intelligence, wherein the previously recorded audio sequence includes a sequence of computer-generated sound signals combined with verbal instructions, wherein the computer-generated sound signals are varied in frequency, sequence, and timing in order to improve the person's cognition and intelligence when the task is performed;
    b) applying stimulus pulses to the person for a first duration of time in synchronization with the playing of the previously recorded audio sequence in step a), wherein the stimulus pulses and the previously recorded audio sequence are in timed correlation; and
    c) applying the stimulus pulses to the person for a second duration of time during the performance of the task to reinforce the memory and effect of the playing of the previously recorded audio sequence, wherein the stimulus pulses are in timed correlation with the previously recorded audio sequence.

2. The method set forth in claim 1, wherein the sequence of computer-generated sound signals are combined with verbal signals.

3. The method set forth in claim 1, wherein the duration of each stimulus pulse is less than one second.

4. The method set forth in claim 1, wherein the stimulus pulses are vibratory pulses emitted by a vibratory device in operative contact with the person.

5. The method set forth in claim 1, wherein the stimulus pulses are light flashes emitted by a light source in a peripheral field of vision of the person.

6. The method set forth in claim 1, wherein the stimulus pulses are auditory sounds emitted by a speaker positioned within a perceptive range of the person.

7. The method as set forth in claim 1, wherein the previously recorded audio sequence in step a) is played by an audio playback device comprising a player device and a speaker device.

8. The method as set forth in claim 7, wherein the speaker device is adapted to be worn by the person as a headset.

9. The method as set forth in claim 1, wherein the stimulus pulses in steps b) and c) are applied to the person using a stimulus presentation device comprising an audio playback device for playing recorded auditory sounds associated with the stimulus pulses, a sound-to-vibration converter for converting the auditory sounds to vibratory stimulus pulses, and a vibratory device adapted for positioning in operative contact with the person for emitting the vibratory stimulus pulses.

10. The method set forth in claim 9, wherein the vibratory device includes at least two vibrators, each vibrator being adapted for positioning in operative contact with the person.

11. The method as set forth in claim 1, wherein the stimulus pulses in steps b) and c) are applied to the person using a stimulus presentation device comprising an audio playback device for playing previously recorded auditory sounds associated with the stimulus pulses, a sound-to-flash converter for converting the auditory sounds to light flash stimulus pulses, and a light source adapted for positioning in a peripheral field of vision of the person for emitting the light flash stimulus pulses.

12. The method set forth in claim 11, wherein the light source includes at least two light emitting diodes (LEDs), each LED being adapted for positioning in a peripheral field of vision of the person.

13. The method set forth in claim 12, wherein the each LED is adapted for attachment to a pair of spectacles worn by the person.

14. The method set forth in claim 1, wherein the stimulus pulses in steps b) and c) are applied to the person using a stimulus presentation device comprising an audio player device for playing previously recorded auditory sounds associated with the stimulus pulses and a speaker device positioned within a perceptive range of the person for emitting the stimulus pulses.

15. The method set forth in claim 1, wherein, during step a), the previously recorded audio sequence is played for a predetermined period of time.

16. The method set forth in claim 1, wherein the stimulus pulses are low frequency signals.

17. A method for improving the cognitive performance and intelligence of a person, the method including the following steps:
   a) playing a previously recorded audio sequence to the person using a first audio playback device prior to the person performing a task requiring cognition and intelligence, the previously recorded audio sequence including a sequence of computer-generated sound signals combined with a verbal signal and verbal instructions, the computer-generated sound signals being varied at least in frequency, sequence, and timing in order to improve the person's cognition and intelligence when the task is performed, the first audio playback device including a player device and a speaker device adapted to be worn by the person as a headset;
   b) applying vibratory stimulus pulses emitted by a stimulus presentation device in operative contact with the person to the person for a first duration of time in synchronization with the playing of the previously recorded audio sequence in step a), the stimulus presentation device including a second audio playback device for playing recorded auditory sounds associated with the stimulus pulses, a sound-to-vibration converter for converting the auditory sounds to vibratory stimulus pulses, and a vibratory device including at least two vibrators, each vibrator being adapted for positioning in operative contact with the person for emitting the vibratory stimulus pulses, the duration of each stimulus pulse being less than one second, the stimulus pulses and the previously recorded audio sequence being in timed correlation; and
   c) applying the vibratory stimulus pulses using the stimulus presentation device to the person for a second duration of time during the performance of the task to reinforce the memory and effect of the playing of the previously recorded audio sequence, the duration of each stimulus pulse being less than one second, the stimulus pulses being in timed correlation with the previously recorded audio sequence.

18. A method for improving the cognitive performance and intelligence of a person, the method including the following steps:
   a) playing a previously recorded audio sequence to the person for a predetermined period of time using a first audio playback device prior to the person performing a task requiring cognition and intelligence, the previously recorded audio sequence including a sequence of computer-generated sound signals combined with a verbal signal and verbal instructions, the computer-generated sound signals being varied at least in frequency, sequence, and timing in order to improve the person's cognition and intelligence when the task is performed, the first audio playback device including a player device and a speaker device adapted to be worn by the person as a headset;
   b) applying stimulus pulses emitted by a stimulus presentation device in operative contact with the person to the person for a first duration of time in synchronization with the playing of the previously recorded audio sequence in step a), the duration of each stimulus pulse being less than one second, the stimulus pulses and the previously recorded audio sequence being in timed correlation; and
   c) applying the stimulus pulses using the stimulus presentation device to the person for a second duration of time during the performance of the task to reinforce the memory and effect of the playing of the previously recorded audio sequence, the duration of each stimulus pulse being less than one second, the stimulus pulses being in timed correlation with the previously recorded audio sequence.

19. The method set forth in claim 18, wherein the stimulus pulses are light flashes and the stimulus presentation device includes a second audio playback device for playing previously recorded auditory sounds associated with the stimulus pulses, a sound-to-flash converter for converting the auditory sounds to light flash stimulus pulses, and a light source including at least two light emitting diodes (LEDs), each LED being adapted for attachment to a pair of spectacles worn by the person in a peripheral field of vision of the person for emitting the light flash stimulus pulses.

20. The method set forth in claim 18, wherein the stimulus pulses are auditory sounds and the stimulus presentation device includes a second audio player device for playing previously recorded auditory sounds associated with the stimulus pulses and a speaker device positioned within a perceptive range of the person for emitting the stimulus pulses.

* * * * *